(12) United States Patent
Sturm et al.

(10) Patent No.: US 7,160,293 B2
(45) Date of Patent: *__Jan. 9, 2007__

(54) MULTIPLE RF RETURN PAD CONTACT DETECTION SYSTEM

(75) Inventors: Thomas A. Sturm, Erie, CO (US); William N. Gregg, Superior, CO (US); Raymond A. Fredricks, Nashua, NH (US)

(73) Assignee: Sherwood Services AG, Schaffhausen (CH)

( * ) Notice: Subject to any disclaimer, the term of this patent is extended or adjusted under 35 U.S.C. 154(b) by 21 days.

This patent is subject to a terminal disclaimer.

(21) Appl. No.: 10/918,984

(22) Filed: Aug. 16, 2004

(65) Prior Publication Data

US 2005/0021022 A1    Jan. 27, 2005

Related U.S. Application Data

(63) Continuation of application No. 10/254,956, filed on Sep. 25, 2002, now Pat. No. 6,860,881.

(51) Int. Cl.
*A61B 18/04* (2006.01)

(52) U.S. Cl. ...................................................... 606/35

(58) Field of Classification Search .............. 606/32–35
See application file for complete search history.

(56) References Cited

U.S. PATENT DOCUMENTS

| | | |
|---|---|---|
| 3,543,760 A | 12/1970 | Bolduc |
| 3,812,861 A | 5/1974 | Peters |
| 3,964,487 A | 6/1976 | Judson |
| 3,987,796 A | 10/1976 | Gonser |
| 4,067,342 A | 1/1978 | Burton |
| 4,092,985 A | 6/1978 | Kaufman |
| 4,114,622 A | 9/1978 | Gonser |

(Continued)

FOREIGN PATENT DOCUMENTS

DE           179607           3/1905

(Continued)

OTHER PUBLICATIONS

Medtrex Brochure "The O.R. Pro 300" 1 p. Sep. 1998.

(Continued)

*Primary Examiner*—Roy D. Gibson

(57) ABSTRACT

A multiple RF return pad contact detection system is provided which is adaptive to different physiological characteristics of patients without being susceptible to electrosurgical current interference (e.g., interference or measurement interaction between components of the detection system). The detection system can measure or sense the contact resistance or impedance between the patient and pairs of RF return pads or return electrodes where multiple pairs of RF return pads are utilized due to the high current frequently needed during electrosurgery while eliminating or minimizing the risk of measurement interaction between the RF return pad pairs. The system allows for the independent and simultaneous measurement of the pad contact impedance for each pair of RF return pads. If the impedance of any pad pair is above a predetermined limit, the system turns off or reduces the electrosurgical output of the electrosurgical generator to prevent excess heating. The system eliminates or minimizes interference or measurement interaction between the pad pairs by providing a different signal source frequency for each pad contact pair, but a frequency which matches an associated series resonant network frequency. The current that flows in the series resonant network is a direct reflection or function of the pad impedance of the corresponding pad pair.

10 Claims, 2 Drawing Sheets

U.S. PATENT DOCUMENTS

| | | |
|---|---|---|
| 4,117,846 A | 10/1978 | Williams |
| 4,121,590 A | 10/1978 | Gonser |
| 4,200,104 A | 4/1980 | Harris |
| 4,213,463 A | 7/1980 | Osenkarski |
| 4,237,887 A | 12/1980 | Gonser |
| 4,253,721 A | 3/1981 | Kaufman |
| 4,303,073 A | 12/1981 | Archibald |
| 4,304,235 A | 12/1981 | Kaufman |
| 4,331,149 A | 5/1982 | Gonser |
| 4,343,308 A | 8/1982 | Gross |
| 4,416,276 A | 11/1983 | Newton et al. |
| 4,416,277 A | 11/1983 | Newton et al. |
| 4,643,193 A | 2/1987 | DeMarzo |
| 4,669,468 A | 6/1987 | Cartmell et al. |
| 4,699,146 A | 10/1987 | Sieverding |
| 4,722,761 A | 2/1988 | Cartmell et al. |
| 4,741,334 A | 5/1988 | Irnich |
| 4,748,983 A | 6/1988 | Shigeta et al. |
| 4,750,482 A | 6/1988 | Sieverding |
| 4,754,757 A | 7/1988 | Feucht |
| 4,768,514 A | 9/1988 | De Marzo |
| 4,799,480 A | 1/1989 | Abraham et al. |
| 4,848,335 A | 7/1989 | Manes |
| 4,873,974 A | 10/1989 | Hagen et al. |
| 4,895,169 A | 1/1990 | Heath |
| 4,947,846 A | 8/1990 | Kitagawa et al. |
| 4,955,381 A | 9/1990 | Way et al. |
| 5,004,425 A | 4/1991 | Hee |
| 5,010,896 A | 4/1991 | Westbrook |
| 5,042,981 A | 8/1991 | Gross |
| 5,087,257 A | 2/1992 | Farin et al. |
| 5,196,008 A | 3/1993 | Kuenecke et al. |
| 5,276,079 A | 1/1994 | Duan et al. |
| 5,362,420 A | 11/1994 | Itoh et al. |
| 5,385,679 A | 1/1995 | Uy et al. |
| 5,388,490 A | 2/1995 | Buck |
| 5,389,376 A | 2/1995 | Duan et al. |
| 5,409,966 A | 4/1995 | Duan et al. |
| 5,496,312 A | 3/1996 | Klicek |
| 5,496,363 A | 3/1996 | Burgio et al. |
| 5,520,180 A | 5/1996 | Uy et al. |
| 5,536,446 A | 7/1996 | Uy et al. |
| 5,540,684 A | 7/1996 | Hassler, Jr. |
| 5,611,709 A | 3/1997 | McAnulty |
| 5,660,892 A | 8/1997 | Robbins et al. |
| 5,670,557 A | 9/1997 | Dietz et al. |
| 5,674,561 A | 10/1997 | Dietz et al. |
| 5,678,545 A | 10/1997 | Stratbucker |
| 5,695,494 A | 12/1997 | Becker |
| 5,696,351 A | 12/1997 | Benn et al. |
| 5,707,369 A | 1/1998 | Vaitekunas et al. |
| 5,720,744 A | 2/1998 | Eggleston et al. |
| 5,766,165 A | 6/1998 | Gentelia et al. |
| 5,779,632 A | 7/1998 | Dietz et al. |
| 5,797,902 A | 8/1998 | Netherly |
| 5,830,212 A | 11/1998 | Cartmell et al. |
| 5,836,942 A | 11/1998 | Netherly et al. |
| 5,846,558 A | 12/1998 | Nielsen et al. |
| 5,853,750 A | 12/1998 | Dietz et al. |
| 5,868,742 A | 2/1999 | Manes et al. |
| 5,924,983 A | 7/1999 | Takaki et al. |
| 5,947,961 A | 9/1999 | Netherly |
| 5,952,398 A | 9/1999 | Dietz et al. |
| 5,961,344 A | 10/1999 | Rosales et al. |
| 5,985,990 A | 11/1999 | Kantner et al. |
| 5,999,061 A | 12/1999 | Pope et al. |
| 6,007,532 A | 12/1999 | Netherly |
| 6,030,381 A | 2/2000 | Jones et al. |
| 6,032,063 A | 2/2000 | Hoar et al. |
| 6,053,910 A | 4/2000 | Fleenor |
| 6,083,221 A | 7/2000 | Fleenor et al. |
| 6,121,508 A | 9/2000 | Bischof et al. |
| 6,162,217 A | 12/2000 | Kannenberg et al. |
| 6,171,304 B1 | 1/2001 | Netherly et al. |
| 6,203,541 B1 | 3/2001 | Keppel |
| 6,214,000 B1 | 4/2001 | Fleenor et al. |
| 6,232,366 B1 | 5/2001 | Wang et al. |
| 6,240,323 B1 | 5/2001 | Calenzo, Sr. et al. |
| 6,258,085 B1 | 7/2001 | Eggleston |
| 6,275,786 B1 | 8/2001 | Daners |
| 6,301,500 B1 | 10/2001 | Van Herk et al. |
| 6,310,611 B1 | 10/2001 | Caldwell |
| 6,347,246 B1 | 2/2002 | Perrault et al. |
| 6,350,264 B1 | 2/2002 | Hooven |
| 6,379,161 B1 | 4/2002 | Ma |
| 6,415,170 B1 | 7/2002 | Loutis et al. |
| 6,454,764 B1 | 9/2002 | Fleenor et al. |
| 6,544,258 B1 | 4/2003 | Fleenor et al. |
| 6,565,559 B1 | 5/2003 | Eggleston |
| 6,582,424 B1 | 6/2003 | Fleenor et al. |
| 6,666,859 B1 | 12/2003 | Fleenor et al. |
| 6,685,701 B1 | 2/2004 | Orszulak et al. |
| 6,796,828 B1 | 9/2004 | Ehr et al. |
| 6,997,735 B1 | 2/2006 | Ehr et al. |
| 2001/0014804 A1 | 8/2001 | Goble et al. |
| 2003/0004510 A1 | 1/2003 | Wham et al. |
| 2003/0139741 A1 | 7/2003 | Goble et al. |
| 2004/0243120 A1 | 12/2004 | Orszulak et al. |
| 2005/0021022 A1 | 1/2005 | Sturm et al. |
| 2005/0079752 A1 | 4/2005 | Ehr et al. |
| 2006/0025760 A1 | 2/2006 | Podhajsky |
| 2006/0030195 A1 | 2/2006 | Ehr et al. |
| 2006/0079872 A1 | 4/2006 | Eggleston |

FOREIGN PATENT DOCUMENTS

| | | |
|---|---|---|
| DE | 1099658 | 2/1961 |
| DE | 1139927 | 11/1962 |
| DE | 1149832 | 6/1963 |
| DE | 1439302 | 1/1969 |
| DE | 2439587 | 2/1975 |
| DE | 2455174 | 5/1975 |
| DE | 2407559 | 8/1975 |
| DE | 2602517 | 7/1976 |
| DE | 2504280 | 8/1976 |
| DE | 2540968 | 3/1977 |
| DE | 2820908 | 11/1978 |
| DE | 2803275 | 8/1979 |
| DE | 2823291 | 11/1979 |
| DE | 2946728 | 5/1981 |
| DE | 3143421 | 5/1982 |
| DE | 3045996 | 7/1982 |
| DE | 3120102 | 12/1982 |
| DE | 3510586 | 10/1986 |
| DE | 3604823 | 8/1987 |
| DE | 390937 | 4/1989 |
| DE | 3904558 | 8/1990 |
| DE | 3942998 | 7/1991 |
| DE | 197 17 411 A1 | 11/1998 |
| DE | 19717411 | 11/1998 |
| DE | 198 01 173 | 7/1999 |
| EP | 246350 | 11/1987 |
| EP | 390937 | 10/1990 |
| EP | 556705 | 8/1993 |
| EP | 0 836 868 | 9/1997 |
| EP | 836868 | 4/1998 |
| EP | 878169 | 11/1998 |
| EP | 1293171 | 3/2003 |
| FR | 1275415 | 10/1961 |
| FR | 1347865 | 11/1963 |
| FR | 2276027 | 6/1974 |
| FR | 2313708 | 12/1976 |

| | | |
|---|---|---|
| FR | 2502935 | 10/1982 |
| FR | 2517953 | 6/1983 |
| FR | 2573301 | 5/1986 |
| GB | 607850 | 9/1948 |
| GB | 902775 | 8/1962 |
| SU | 166452 | 1/1965 |
| SU | 727201 | 4/1980 |
| WO | WO 98/18395 | 5/1998 |
| WO | WO 99/11187 | 3/1999 |
| WO | WO 00/32122 | 6/2000 |
| WO | WO 00/53113 | 9/2000 |
| WO | WO 01/87175 | 11/2001 |
| WO | WO02/011634 | 2/2002 |
| WO | WO02/045589 | 6/2002 |
| WO | WO02/088128 | 7/2002 |
| WO | WO 02/058579 | 8/2002 |
| WO | WO 02/060526 | 8/2002 |
| WO | WO 03/094766 | 11/2003 |
| WO | WO 05/048809 | 6/2005 |

OTHER PUBLICATIONS

Valleylab Brochure "Valleylab Electroshield Monitoring System" 2 pp. Nov. 1995.
Richard Wolf Medical Instruments Corp. Brochure, "Kleppinger Bipolar Forceps & Bipolar Generator" 3 pp. Jan. 1989.
International Search Report PCT/US03/37110 dated Jul. 25, 2005.
International Search Report PCT/US03/37310 dated Aug. 13, 2004.
International Search Report EP 04009964 dated Jul. 13, 2004.
International Search Report EP 98300964.8 dated Dec. 4, 2000.
International Search Report EP 04015981.6 dated Sep. 29, 2004.
International Search Report EP 05014156.3 dated Dec. 28, 2005.
International Search Report EP 05021944.3 dated Jan. 18, 2006.
International Search Report EP 05022350.2 dated Jan. 18, 2006.
International Search Report EP 05021944.3 dated Jan. 25, 2006.
International Search Report EP 05002027.0 dated May 12, 2005.
International Search Report from EP 06006961 dated Aug. 3, 2006.

MULTIPLE RF RETURN PAD CONTACT DETECTION SYSTEM

CROSS-REFERENCE TO RELATED APPLICATION

The present application is a continuation application which claims the benefit of and priority to U.S. application Ser. No. 10/254,956, filed on Sep. 25, 2002, now U.S. Pat. No. 6,860,881, the entire contents of which are herein incorporated by reference.

BACKGROUND

1. Technical Field

The present disclosure is directed to electrosurgery and, in particular, to circuitry for measuring or sensing the contact resistance or impedance between the patient and pairs of RF return pad contacts or electrodes employed in such surgery.

2. Description of the Related Art

One potential risk involved in electrosurgery is the possibility of stray electrical currents causing excess heating proximate the RF return pad contacts or patient return electrodes. The most common conditions which are thought to lead to excess heating include:

(1) Tenting: Lifting of the return electrode from the patient due to patient movement or improper application. This situation may lead to excess heating if the area of electrode-patient contact is significantly reduced;

(2) Incorrect Application Site: Application of a return electrode over a highly resistive body location (e.g., excessive adipose tissue, scar tissue, erythema or lesions, excessive hair) will lead to a greater, more rapid temperature increase. Or, if the electrode is not applied to the patient (i.e. electrode hangs freely or is attached to another surface), the current may seek an alternate return path such as the table or monitoring electrodes; and (3) Gel drying either due to premature opening of the electrode pouch or use of an electrode which has exceeded the recommended shelf life.

Many monitor or detection systems have been developed in the past, but most cannot directly guard against all three of the above listed situations. In order to protect against these potentially hazardous situations, the contact resistance or impedance between the return electrode and the patient should be monitored in addition to the continuity of the patient return circuit.

Safety circuitry is known whereby split (or double) patient electrodes are employed and a DC current (see German Pat. No. 1,139,927, published Nov. 22, 1962) or an AC current (see U.S. Pat. Nos. 3,933,157 and 4,200,104) is passed between the split electrodes to sense the contact resistance or impedance between the patient and the electrodes. U.S. Pat. No. 3,913,583 discloses circuitry for reducing the current passing through the patient depending upon the area of contact of the patient with a solid, patient plate. A saturable reactor is included in the output circuit, the impedance of which varies depending upon the sensed impedance of the contact area.

The above systems are subject to at least one or more of the following shortcomings:

(a) lack of sensitivity or adaptiveness to different physiological characteristics of patients and (b) susceptibility to electrosurgical current interference when monitoring is continued during electrosurgical activation.

U.S. Pat. Nos. 4,416,276 and 4,416,277 describe a split-patient return electrode monitoring system which is adaptive to different physiological characteristics of patients, and a return electrode monitoring system which has little, if any, susceptibility to electrosurgical current interference when monitoring is continued during electrosurgical activation. The entire contents of both U.S. Pat. Nos. 4,416,276 and 4,416,277 are incorporated herein by reference.

Still a need exists for a detection or monitoring system, which is: 1) adaptive to different physiological characteristics of patients; 2) has little, if any, susceptibility to electrosurgical current interference, (including interference or measurement interaction between components of the detection system); 3) can measure or sense the contact resistance or impedance between the patient and pairs of RF return pads or electrodes where multiple pairs of RF return pads are utilized due to the high current frequently needed during electrosurgery, such as during tissue ablation; and 4) eliminates or minimizes the risk of measurement interaction between the RF return pad pairs.

Therefore, it is an aspect of the invention to provide a multiple RF return pad contact detection system for use during electrosurgical activation which achieves the above objectives.

SUMMARY

A multiple RF return pad contact detection system is disclosed which is adaptive to different physiological characteristics of patients, without being susceptible to electrosurgical current interference. The detection system includes interference or measurement interaction between components of the detection system which can measure or sense the contact resistance or impedance between the patient and pairs of RF return pads or electrodes when multiple pairs of RF return pads are utilized. Due to the high current frequently needed during electrosurgery, such as during tissue ablation, the detection system eliminates or minimizes the risk of measurement interaction between the RF return pad pairs.

The circuitry of the multiple RF return pad contact detection system is preferably provided within an electrosurgical generator for controlling the generator according to various measurements, such as the contact resistance or impedance between the patient and pairs of RF return pads or return electrodes. The system allows for the independent and simultaneous measurement of the pad contact impedance for each pair of RF return pads. If the impedance of any pad pair is above a predetermined limit, the system turns off or reduces the electrosurgical output of the electrosurgical generator to prevent excess heating.

The system eliminates or minimizes interference or measurement interaction between the pad pairs by providing a different signal source frequency for each pad contact pair, but a frequency which matches an associated series resonant network frequency. The current that flows in the series resonant network is a direct reflection or function of the pad impedance of the corresponding pad pair. Since the two resonant networks are tuned to different frequencies, there is minimal interaction, if any, within the system, thus reducing the chances of inaccurate measurements.

The system could be modified by providing a multiplexer to multiplex the measurements corresponding to each pad contact pair to eliminate or minimize measurement interaction and also minimize hardware resources.

Further features of the multiple RF return pad contact detection system of the invention will become more readily apparent to those skilled in the art from the following detailed description of the apparatus taken in conjunction with the drawing.

BRIEF DESCRIPTION OF THE DRAWINGS

Various embodiments of the invention will be described herein below with reference to the drawings wherein.

DETAILED DESCRIPTION OF PREFERRED EMBODIMENTS

Figure 1:
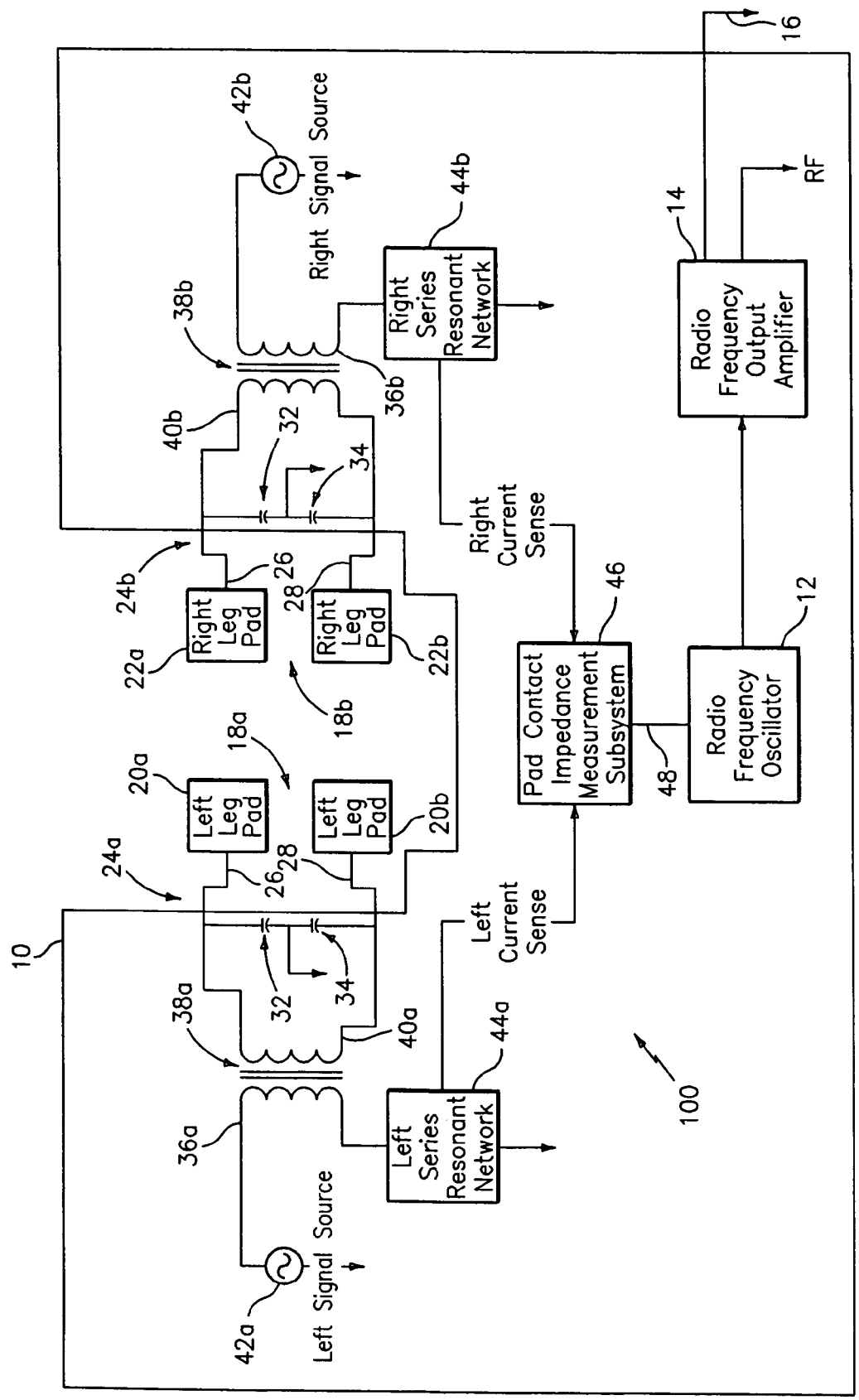
FIG. 1 is a schematic diagram of the multiple RF return pad contact detection system in accordance with a preferred embodiment of the invention.

Reference should be made to the drawings where like reference numerals refer to similar elements. Referring to FIG. 1, there is shown a schematic diagram of the multiple RF return pad contact detection system 100 of the present invention wherein electrosurgical generator 10 includes known circuitry such as a radio frequency oscillator 12 and an output amplifier 14 which generate an electrosurgical current. This current is applied to a patient (not shown) via an active electrode 16. The electrosurgical current is returned to the generator 10 via pad contact pairs or return electrode pairs 18a, 18b having pads or electrodes 20a, 20b and 22a, 22b and a corresponding two conductor patient cable 24a, 24b having leads 26 and 28. Two capacitors 32 and 34 are connected across each of the secondary windings 40a, 40b of transformer 38a, 38b.

Each primary winding 36a, 36b is connected to a corresponding a.c. signal source 42a, 42b and a series resonant network 44a, 44b. The purpose of each series resonant network 44a, 44b is to produce a current (i.e., left and right current senses) which is a function of the impedance between pads or electrodes 20a, 20b and 22a, 22b.

The system 100 eliminates or minimizes interference or measurement interaction between the pads 20a, 20b and 22a, 22b, while allowing for the independent and simultaneous measurement of the pad contact impedance for each pair of RF return pads by having each a.c. signal source 42a, 42b provide a different signal source frequency for its corresponding pad contact pair. The frequency of each series resonant network 44a, 44b is tuned to match the frequency of the current produced by its associated a.c. signal source 42a, 42b.

Accordingly, the frequency of one of the series resonant networks 44a is different from the frequency of the other series resonant network 44b. Hence, there is minimal interaction, if any, between the left and right circuitry of the system 100, especially the two contact pad pairs 18a, 18b. This essentially eliminates inaccurate or confusing measurements.

Additionally, the frequency of the electrosurgical current produced by the electrosurgical generator 10 is substantially different from that of the current produced by the a.c. signal sources 42a, 42b.

The current that flows in each series resonant network 44a, 44b, i.e., left and right current senses, is a direct reflection or function of the pad impedance of the corresponding pad contact pair 18a, 18b according to the physics of a series resonant network. Each series resonant network 44a, 44b is an RCL network or a combination of R (resistance), L (inductance) and C (capacitance). In a preferred embodiment of the series resonant networks 44a, 44b, the inductive component for each network is integrated into the respective transformer 38a, 38b.

The frequency response of a series resonant network has a maximum resonant frequency $f_R$. At the resonant frequency, the series resonant network has the minimum impedance, as opposed to a parallel resonant network which has the maximum impedance at the resonant frequency, and the phase angle is equal to zero degrees. The total impedance of a series resonant network is $Z_T+jX_L-jX_C=R+j(X_L-X_C)$. At resonance: $X_L=X_C$, $f_R=1/(2\pi\sqrt{LC})$, $Z_T=R$, and $V_L=V_C$. The resonance of a series resonant network occurs when the inductive and capacitive reactances are equal in magnitude but cancel each other because they are 180 degrees apart in phase.

The left and right current senses are applied to pad contact impedance measurement subsystem 46 which determines whether the impedance measurements between pads or return electrodes 20a, 20b and 22a, 22b are within a desired range. The range is preferably adaptable to the physiological characteristics of the patient. If at least one of the impedance measurements is not within a desired range, an inhibit signal is applied over a line 48 to internally disable the electrosurgical generator 10 (or reduce the RF output therefrom) to prevent excess heating.

U.S. Pat. Nos. 4,416,276 and 4,416,277 describe a method for determining the desired range according to the physiological characteristics of the patient, the entire contents of these patents is incorporated herein by reference.

Preferably, the desired range for which the impedance must fall between return electrodes 20a, 20b and 22a, 22b is about 20 to about 144 ohms. If not, the electrosurgical generator 10 is disabled. Thus, in one method of operation of the present invention, the lower limit is fixed at the nominal value of 20 ohms, thus reducing the onset of patient injury as a result of stray current paths which may surface if a contact pad or electrode is applied to a surface other than the patient. The upper limit is set to avoid such problems as those mentioned hereinbefore, i.e., tenting, incorrect application site, gel drying, etc.

In accordance with an important aspect of the invention, the upper limit is adjustable from the absolute maximum (typically about 144 ohms) downward to as low as typically 20 ohms to thereby provide for automatic adaptiveness to the physiological characteristics of the patient. This provides the multiple RF return pad contact detection system 100 of the present invention with significantly more control over the integrity of the RF pad contact or electrode connections without limiting the range of patient types with which the multiple RF return pad contact detection system 100 may be used or burdening the operator with additional concerns.

That is, the physiological characteristics can vary significantly from patient to patient and from one location site for the pad pairs to another. Thus, patients may vary in their respective amounts of adipose tissue (which is one determining factor in the impedance measurement between the various pads) without effecting the detection system. Further, for a particular patient, one location site may be more fatty, hairy or scarred than another. Again, this does not reduce the effectiveness of the system, i.e., all of these factors typically affect the impedance measured between pads 20a, 20b and 22a, 22b and thus concern the operator as to which site is optimal for a particular patient. Such concerns are eliminated in accordance with the present invention by providing for automatic adaptability to the physiological characteristics of the patient.

Figure 2:
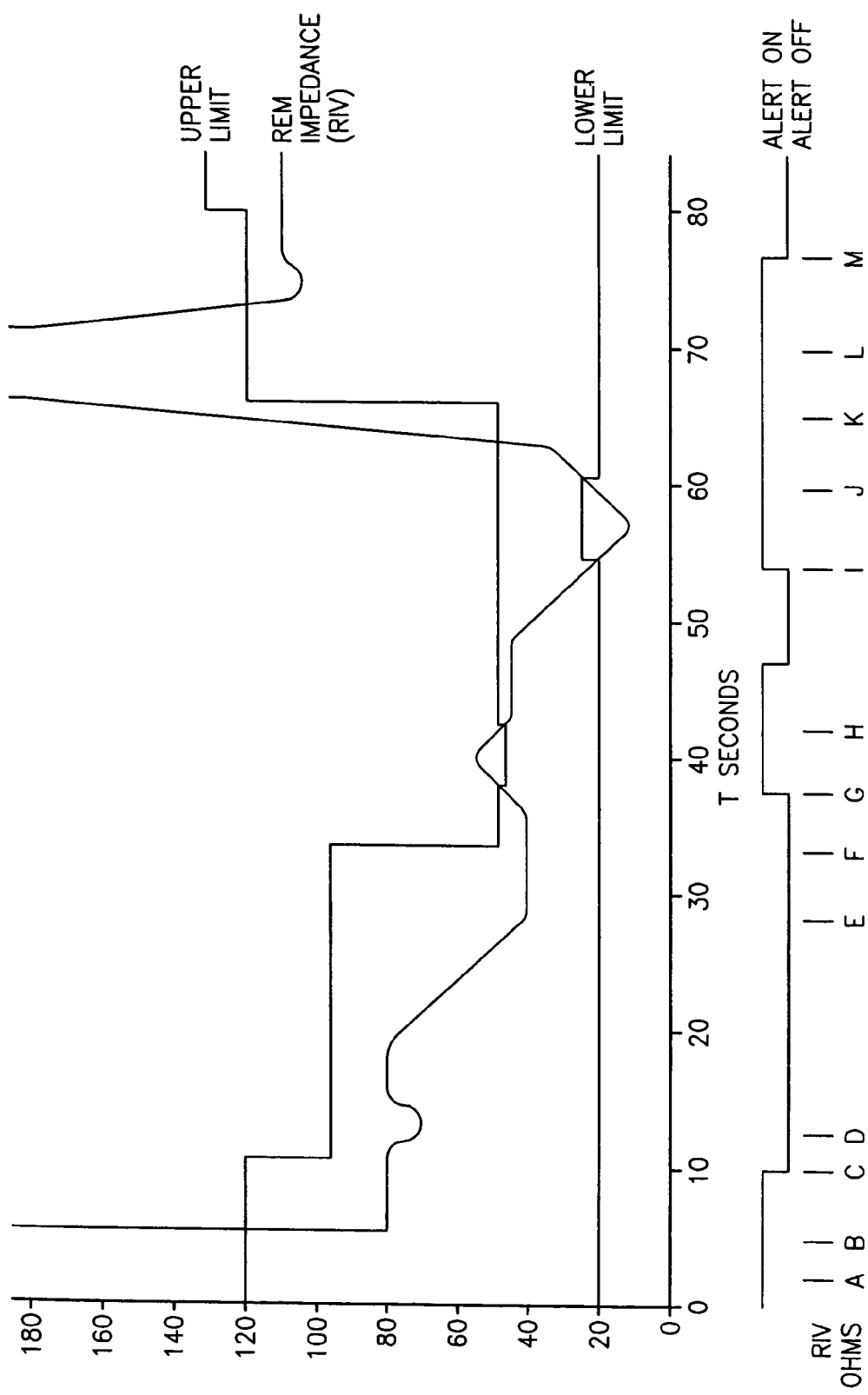
FIG. 2 is a graph illustrating the operation of the pad contact impedance measurement subsystem of FIG. 1.

Reference should now be made to FIG. 2 which is a graph illustrating the operation of pad contact impedance measurement subsystem 46.

During operation, the desired impedance range (that is, the acceptable range of the impedance detected between pads 20a, 20b and 22a, 22b) is preset when the power is turned on to an upper limit of, for example, 120 ohms and a lower limit of, for example, 20 ohms as can be seen at time T=0 seconds in FIG. 2. If the monitored impedance for any pad contact pair is determined to be outside of this range (T=A seconds) by comparing the current sense signal (or a signal derived there from) with a reference signal (e.g., a signal equal to 120 ohms or 20 ohms) using comparator circuitry (e.g., when a pad pair or any single contact pad is not affixed to the patient) an alert will be asserted and the electrosurgical generator 10 will be disabled over line 48.

The impedance between two contact pads of a contact pad pair at any instant is designated the return RF electrode monitor (REM) Instantaneous Value (RIV) in FIG. 2. When the REM impedance enters the range (T=B seconds) bounded by the Upper Limit (UL) and the Lower Limit (LL), a timing sequence begins. If after five seconds the RIV is still within range (T=C seconds), the alert condition will cease and the REM impedance value is stored in memory. This is designated as REM Nominal Value (RNV). The upper limit is then reestablished as 120% of this amount. The 80 ohm RIV shown in FIG. 2 causes the upper limit to be at 96 ohms. This feature of the invention is particularly important because it is at this time (T=C seconds) that adaptation is initially made to the physiological characteristics of the patient. Note if the RIV were to exceed 96 ohms at a time between T=C and T=F seconds (while the upper limit is 96 ohms), the alert will be asserted and the electrosurgical generator 10 disabled.

However, if the upper limit had not been adjusted to 96 ohms, the alert would not have been asserted until after the RIV exceeded the initial 120 ohms upper limit as determined by the comparator circuitry, thus possibly heating one or both of the pads 20a, 20b and 22a, 22b. This situation is of course exacerbated if the patient's initial RIV within the preset 20 to 120 ohm range is 30 ohms.

An initial RIV of 10 ohms within the preset range of 20 to 120 ohms sets an upper limit of 144 ohms.

In accordance with another aspect of the invention, it has been observed that the impedance between contact pads of contact pad pairs decreases over a relatively long period, such as a number of hours. Since many surgical procedures can extend a number of hours, this effect is also taken into consideration in the present invention. Accordingly, RIV is continuously monitored and any minima in REM impedance (e.g., a downward trend followed by a constant or upward trend in REM impedance) initiates a new five second timing interval (T=E seconds) at the end of which the RNV is updated to the RIV if the RIV is lower (T=F seconds). The REM upper limit of 120% of RNV is re-established at this time. The five second interval causes any temporary negative change in REM impedance (T=D seconds) to be disregarded. Operation will continue in this manner provided RIV does not exceed the upper limit of 120% RNV or drop below the lower limit of 20 ohms. Exceeding the upper limit (T=G seconds) causes an alert and the electrosurgical generator 10 is disabled. It will remain in alert until the RIV drops to 115% of RNV or less (T=H seconds) or until the system 100 is reinitialized. RIV dropping to less than 20 ohms (T=I seconds) causes a similar alert which continues until either the RIV exceeds 24 ohms (T=J seconds) or the system 100 is reinitialized. The hysteresis in the limits of the REM range (that is, the changing of the upper limit to 115% of RNV and the lower limit to 24 ohms in the previous examples) prevents erratic alerting when RIV is marginal.

It should be noted in the example of FIG. 2 that the alert actually does not turn off when RIV returns to a value greater than 24 ohms because the pad pairs are removed before 5 seconds after T=J seconds elapse. Thus, the alarm stays on due to the removal of the pad contact pairs 18a, 18b.

Removing the pad contact pairs 18a, 18b from the patient or unplugging the cables 26, 28 from the electrosurgical generator 10 (T=K seconds) for more than one second causes the system 100 to be reinitialized to the original limits of 120 and 20 ohms. This permits a pad to be relocated or replaced (T=L seconds) without switching the electrosurgical generator 10 off. The RIV at the new location is 110 ohms and 120% RNV is 132 ohms. Thus, as described above, this is the one time (whenever RIV enters the 20 to 120 ohms range (either as preset during power on or as reinitialized as at T=K seconds) for the first time) that the upper limit can be raised during the normal REM cycle. Otherwise, it is continually decreased to adapt to the decreasing RIV impedance with the passage of time.

The preferred implementation of the foregoing FIG. 2 operation of the pad contact impedance measurement subsystem 46 is effected by a set of programmable instructions configured for execution by a microprocessor.

The system 100 could be modified by providing a multiplexer to multiplex the measurements corresponding to each pad contact pair 18a, 18b to eliminate or minimize measurement interaction and also minimize hardware resources.

Other pad contact pair arrangements can be provided in the system 100 of the present invention besides the pad pair arrangements shown in FIG. 1. For example, ten pad contact pairs 18 can be provided and connected to electrosurgical generator 10 by cables 26 and 28, where the corresponding a.c. signal source 42 and series resonant network 44 corresponding to each pad contact pair 18 are tuned to the same frequency which is different from the frequency of the other a.c. signal sources 42 and series resonant networks 44.

It is provided that the system 100 of the present invention allows for impedance comparisons to be performed between pad pairs. Therefore, if the pad pairs are placed symmetrically on the patient, i.e., left leg and right leg, comparison of the contact impedance can provide another degree of detection and safety.

Although the subject apparatus has been described with respect to preferred embodiments, it will be readily apparent to those having ordinary skill in the art to which it appertains that changes and modifications may be made thereto without departing from the spirit or scope of the subject apparatus.

What is claimed is:

1. In an electrosurgical generator including at least two pairs of patient return pads adapted for contacting a patient, each pair of said at least two pairs of patient return pads having two conductors attached to a corresponding patient return pad for connecting the pad to a source of a.c. energy passing through the pad, a method for controlling the electrosurgical generator comprising the steps of:

producing and applying a corresponding current signal for each of said at least two pairs of patient return pads;

producing at least one signal by resonant circuitry means responsive to the impedance between at least one pair of patient return pads; and receiving said at least one signal for determining the impedance between said at least one pair of patient return pads, wherein the frequency of said corresponding current signal for each of said at least two pairs of patient return pads is substantially equal to the frequency of at least a portion of said resonant circuitry means.

2. The method as in claim 1, wherein said resonant circuitry means includes at least two RCL series resonant circuits having minimum impedance at the resonant frequency and wherein each of said at least two resonant circuits being tuned to different frequencies.

3. The method as in claim 1, further comprising the steps of:
establishing a desired range having at least an upper limit for said impedance; and
determining whether said impedance is within said desired range.

4. The method as in claim 3, wherein said establishing a desired range step includes generating a first reference signal corresponding to the upper limit and wherein said determining step includes comparing said at least one signal which is a function of said impedance with the first reference signal.

5. The method as in claim 4, further comprising the step of generating a control signal for controlling the operation of said electrosurgical generator according to the determination made by said comparing step.

6. The method as in claim 4, wherein said desired range includes a lower limit for said impedance, further comprising the step of generating a second reference signal corresponding to the lower limit and wherein said determining step includes comparing said at least one signal which is a function of said impedance with the first and second reference signals.

7. The method as in claim 6, further comprising the step of generating a control signal for controlling the operation of said electrosurgical generator according to the determination made by said comparing step.

8. The method as in claim 6, wherein the lower limit for said impedance is about 20 ohms and the upper limit for said impedance is about 144 ohms.

9. The method as in claim 2, further comprising the step of generating electrosurgical current at a frequency substantially different from that of said corresponding current signal.

10. In an electrosurgical generator including at least two pairs of patient return pads adapted for contacting a patient, each pair of said at least two pairs of patient return pads having two conductors attached to a corresponding patient return pad for connecting the pad to a source of a.c. energy passing through the pad, a method for controlling the electrosurgical generator comprising the steps of:
generating an operating current for each pair of said at least two pairs of patient return pads, each pair of said at least two pairs of patient return pads having a corresponding signal source;
applying the operating current through said conductors to said at least two pairs of patient return pads;
producing a signal for each pair of patient return pads responsive to said current which is a function of the impedance between said two corresponding patient return pads via resonant circuits corresponding to each pair of return pads, said each resonant circuit being tuned to different frequencies and being tuned to the substantially the same frequency as the corresponding signal source for substantially minimizing measurement interaction between the at least two pairs of patient return pads when said operating currents are simultaneously applied to said corresponding pairs of patient return pads; and
determining whether said signals produced are within a desired range of impedance.

* * * * *